United States Patent
Iwaki et al.

(10) Patent No.: US 6,180,673 B1
(45) Date of Patent: Jan. 30, 2001

(54) CORNEAL SUBEPITHELIAL OPACITY (HAZE) INHIBITOR

(75) Inventors: Yoichi Iwaki; Ikuo Tobari; Susumu Okamoto; Tatsuro Sakai, all of Tokyo (JP)

(73) Assignees: Kissei Pharmaceutical Co., Ltd.; Nihon Tenganyaku Co., Ltd., both of (JP)

( * ) Notice: Under 35 U.S.C. 154(b), the term of this patent shall be extended for 0 days.

(21) Appl. No.: 09/269,161

(22) PCT Filed: Sep. 24, 1997

(86) PCT No.: PCT/JP97/03371

§ 371 Date: Mar. 23, 1999

§ 102(e) Date: Mar. 23, 1999

(87) PCT Pub. No.: WO98/13038

PCT Pub. Date: Apr. 2, 1998

(30) Foreign Application Priority Data

Aug. 28, 1996 (JP) .................................................. 8-292222

(51) Int. Cl.$^7$ ................................................. A61K 31/195
(52) U.S. Cl. ............................................................ 514/563
(58) Field of Search ................................................. 514/563

(56) References Cited

U.S. PATENT DOCUMENTS 5,223,639 * 6/1993 Satou .................................... 562/455
5,356,620 * 10/1994 Yammamoto et al. ........... 424/78.04

* cited by examiner

Primary Examiner—Raymond Henley, III
(74) Attorney, Agent, or Firm—Stuart D. Frenkel

(57) ABSTRACT

The present invention relates to a corneal subepithelial opacity (haze) inhibitor comprising as the active ingredient N-(3,4-dimethoxycinnamoyl)anthranilic acid represented by the formula:

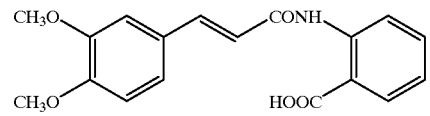

or a pharmaceutically acceptable salt thereof, is useful for the prevention or treatment of corneal subepithelial opacity (haze) caused by a wound during the operation of refractive surgery such as keratectomy and radial keratotomy, and an external wound.

6 Claims, 1 Drawing Sheet

CORNEAL SUBEPITHELIAL OPACITY (HAZE) INHIBITOR

This is a 371 of PCT/JP97/03371 filed Sept. 24, 1997.

FIELD OF THE INVENTION

The present invention relates to a corneal subepithelial opacity (haze) inhibitor which comprises as the active ingredient N-(3,4-dimethoxycinnamoyl)anthranilic acid (generic name: Tranilast) represented by the formula:

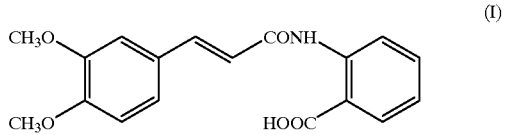

(I)

or a pharmaceutically acceptable salt thereof.

More particularly, the present invention relates to an inhibitor of corneal subepithelial opacity (haze) caused by an injury to the cornea, which inhibitor comprises as the active ingredient Tranilast or a pharmaceutically acceptable salt thereof.

In the present invention, examples of an injury to the cornea include, a wound occuring during refractive surgery such as keratectomy and radial keratotomy, an external wound, other physical injuries to the cornea and the like.

BACKGROUND OF THE INVENTION

In the ophthalmic field, refractive surgery such as keratectomy and radial keratotomy has recently received public attention. The surgical treatment to correct vision is extremely useful in that permanent vision correction can be realized in comparison with conventional correction methods using compensating lenses such as eye glasses and contact lenses.

Radial keratotomy (RK) is a surgical treatment which involves the placement of radial incisions extending outwardly from the center of the cornea with a surgical knife. In general, the number of incision lines is in the range of 4–12 and the depth of the cutting is about 90 to 95% of the corneal thickness. However, when performing this procedure, it is very difficult to place the cuts uniformly. Corneal degeneration after the surgery has become a problem. Accordingly, to solve the above problems found in keratotomy using a surgical knife, keratectomy using a laser was designed.

Keratectomy using an excimer laser can be divided into photo refractive keratectomy (PRK) and phototherapeutic keratectomy (PTK). As an example of keratectomy for either procedure, optical keratectomy using an ultraviolet laser having a wavelength about 193 nm can be illustrated. Hundreds of thousands of patients have already undergone excimer laser treatment all over the world. In the United States of America, this procedure for curing myopia received FDA approval in October of 1995. Photorefractive keratectomy is employed for curing or improving paropsia, for example, correcting ametropia such as myopia, hyperopia and astigmatism. Phototherapeutic keratectomy is useful for treating opacity regions in the corneal surface associated with corneal degeneration etc.

However, because these surgical methods involve incision or excision of the cornea, in almost all cases corneal subepithelial opacity (haze) will occur at the site of incision or laser application during the wound-healing stage. Especially, because keratectomy involves removal of the central corneal epithelium, there is a serious problem that corneal subepithelial opacity (haze) after the surgery leads to visual dysfunction such as lower vision, glare and regression. However, the mechanism of corneal subepithelial opacity (haze) has not yet been clearly elucidated. In general, corneal subepithelial opacity (haze) is usually transitory. Namely, corneal subepithelial opacity (haze) is not observed immediately after the surgery and occurs from 2 weeks to 1 month after the surgery, i.e., the time that the corneal epithelium has nearly rehealed. Subsequently, the opacity peaks in 2–3 months after the surgery and disappears generally at about 6 months to 1 year after the surgery. Occasionally, the cornea is not completely cured and the opacity remains.

At the present time, on the hypothesis that collagen accumulation plays more than a small part in corneal subepithelial opacity (haze) after excimer laser application, eye drops containing a steroid which has inhibitory activities on fibroblast cell proliferation and collagen accumulation and which is used for the treatment of keloid etc., have been used as therapeutic agents for curing corneal subepithelial opacity (haze). However, it has been reported that steroids delay rehealing of the corneal epithelium because of uncertain effects and that side effects such as glaucoma occur occasionally. Furthermore, it has been reported that instillation on the eyes of fluorouracil, an anticancer medicine, and heparin, an anticoagulant, had no therapeutic effect. Thus, corneal subepithelial opacity (haze) occurs in the eye, which is distinctive and is greatly different from the other organs and tissues. Therefore, corneal subepithelial opacity (haze) differs from diseases occurring in other organs and as such therapeutic agents capable of effectively treating diseases which result in cell proliferation or collagen accumulation do not show favorable effects on corneal subepithelial opacity (haze). Hence, satisfactory corneal subepithelial opacity (haze) inhibitors have not yet been developed.

Accordingly, development of inhibitors of corneal subepithelial opacity (haze) caused by an injury to the cornea has been desired for accelerating the healing of a wound such as occurs after keratectomy using an excimer laser etc. or radial keratotomy, or of external wound or other physical injury and for improving visual dysfunction such as lower vision.

Tranilast has been widely used as an internal medicine or in eye drops for the treatment of allergic disorders such as bronchial asthma, allergic rhinitis, atopic dermatitis and allergic conjunctivitis, and cutaneous disorders such as keloid and hypertrophic scar. For example, it has been known that Tranilast has inhibitory activities on chemical mediator release caused by an allergic reaction, excessive collagen accumulation by fibroblast cells in cutaneous tissues and excessive proliferation of smooth muscle cells in coronary artery vessels.

However, it is not known that Tranilast suppresses corneal subepithelial opacity (haze) such as caused by an injury to the cornea.

SUMMARY OF THE INVENTION

The present invention relates to a corneal subepithelial opacity (haze) inhibitor which comprises as the active ingredient N-(3,4-dimethoxycinnamoyl)anthranilic acid represented by the formula:

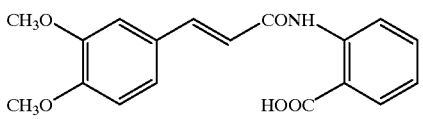

(I)

or a pharmaceutically acceptable salt thereof.

The present invention relates to a method for the prevention or treatment of corneal subepithelial opacity (haze) which comprises administering N-(3,4-dimethoxycinnamoyl)-anthranilic acid represented by the above formula (I) or a pharmaceutically acceptable salt thereof.

The present invention relates to a use of N-(3,4-dimethoxycinnamoyl)anthranilic acid represented by the above formula (I) or a pharmaceutically acceptable salt thereof for the manufacture of a pharmaceutical composition for the prevention or treatment of corneal subepithelial opacity (haze)

Furthermore, the present invention relates to a use of N-(3,4-dimethoxycinnamoyl)anthranilic acid represented by the above formula (I) or a pharmaceutically acceptable salt thereof as a corneal subepithelial opacity (haze) inhibitor.

DETAILED DESCRIPTION OF THE INVENTION

Figure 1:
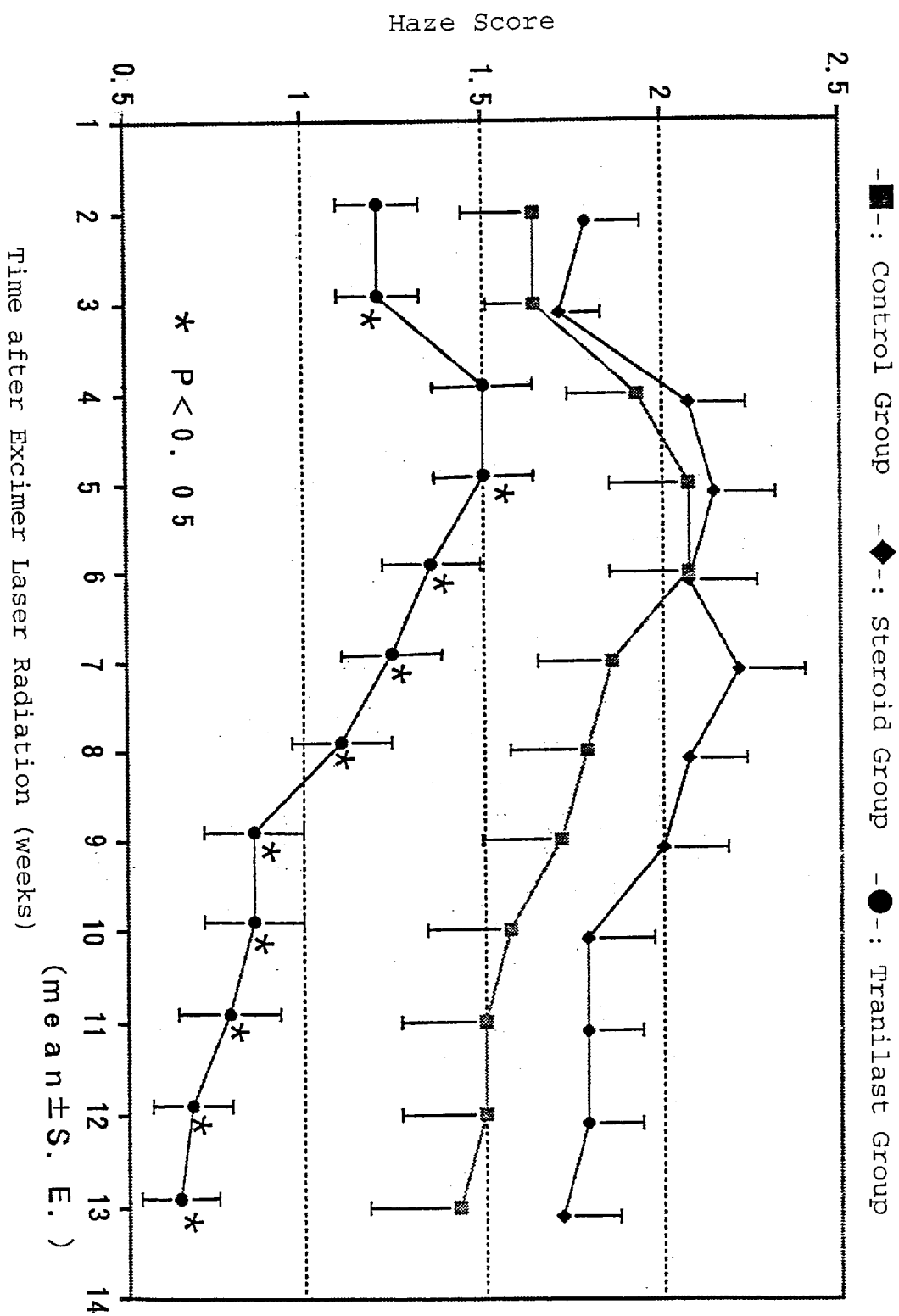
FIG. 1 is a graph illustrating results from the Example of in vivo test for suppressing corneal subepithelial opacity (haze) using rabbits. The axis of the ordinates shows haze score, and the axis of the abscissas shows time after excimer laser radiation (weeks). The symbols —■—, —●—, and —◆— in the graph show the control group, Tranilast group and steroid group, respectively.

The present inventors have extensively studied to find compounds which have an inhibitory activity on corneal subepithelial opacity (haze) caused by an injury to the cornea. As a result, it was found that Tranilast has a marked inhibitory effect on corneal subepithelial opacity (haze) after excimer laser keratectomy, and is extremely useful as a corneal subepithelial opacity (haze) inhibitor, thereby forming the basis of the present invention.

Tranilast was instilled on rabbit eyes radiated with an excimer laser, and the degree of corneal subepithelial opacity (haze) at 2–13 weeks after the radiation was observed. As a result, the present inventors confirmed that corneal subepithelial opacity (haze) in the group treated with Tranilast had been significantly suppressed in comparison with that in the control group not treated with Tranilast.

Thus it has been shown that Tranilast has an extremely excellent inhibitory effect on corneal subepithelial opacity (haze) associated with keratectomy, and therefor, is a useful compound as a corneal subepithelial opacity (haze) inhibitor.

Therefore, pharmaceutical compositions which are useful as a corneal subepithelial opacity (haze) inhibitor can be prepared by comprising as the active ingredient Tranilast or a pharmaceutically acceptable salt thereof.

Various methods for the preparation of Tranilast and salts thereof are known (Japanese Patent Application Publication (kokoku) No.Sho.56-40710; ibid. No.Sho.57-36905; ibid. No.Sho. 58-17186; ibid. No.Sho.58-48545; ibid. No.Sho.58-55138; ibid. No.Sho.58-55139; ibid. No.Hei.01-28013; ibid. No.Hei.01-50219; ibid. No.Hei.03-37539 etc.). For example, Tranilast and pharmaceutically acceptable salts thereof can be prepared by allowing a reactive functional derivative such as an acid halide or an acid anhydride of 3,4-dimethoxycinnamic acid represented by the formula:

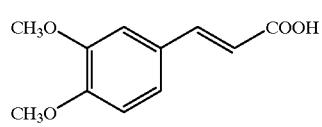

(II)

to react with anthranilic acid represented by the formula:

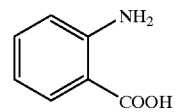

(III)

in the usual way, and if desired, converting the resulting compound into a salt thereof.

As examples of pharmaceutically acceptable salts of Tranilast, salts with inorganic bases such as a sodium salt and a potassium salt, salts formed with organic amines such as morpholine, piperazine and pyrrolidine and salts formed with amino acids can be illustrated.

The pharmaceutical compositions of the present invention can be employed during treatment, by oral administration, but topical application with eye drops, eye ointments or the like is preferred.

For example, eye drops of the present invention can be formulated by dissolving Tranilast or a pharmaceutically acceptable salt together with a basic compound with heating in sterilized water in which a surface active agent is dissolved, adding polyvinylpyrrolidone, optionally adding appropriate pharmaceutical additives such as a preservative, a stabilizing agent, a buffer, an isotonicity, an antioxidant and a viscosity improver, and dissolving completely.

Eye ointments of the present invention can be prepared by employing a base material generally used in eye ointments.

When the pharmaceutical compositions of the present invention are employed in practical treatment, the dosage of Tranilast or a pharmaceutically acceptable salt thereof as the active ingredient is appropriately decided based on the age, degree of symptoms and treatment etc. of each patient and may be fixed within the concentration at which medical value is attained.

For example, eye drops, containing preferably 0.001–2 weight % Tranilast, can be instilled 1 to several times per day and applied 1 to several droplets per time.

The dose of Tranilast or a pharmaceutically acceptable salt thereof can be appropriately increased or decreased depending on the type of diseases, and degree of symptoms of each patient to be treated and the therapeutic value.

The present invention is further illustrated in more detail by way of the following Example.

Example

In vivo experiment for suppressing corneal subepithelial opacity (haze)

An excimer laser was radiated to both eyes of colored rabbits (Dutch) of 22—22 weeks age under the following condition. After the radiation, the rabbits were divided into 3 groups (n=7). Each group was respectively instilled with eye drops containing 0.5% Tranilast (Tranilast group), 0.1% betamethasone sodium phosphate (steroid group) or a base materiel (control group) 4 times per day, 50 μl per time for 13 consecutive weeks. The efficacy of suppressing corneal subepithelial opacity (haze) was ophthalmoscopically evaluated according to the following Fantes' classification.

Excimer laser-radiating condition
Application of excimer laser: MINI-EXCIMER COMPAK-200 (LASER SIGHT)

Radiation energy: 0.90 mJ/pulse

Frequency: 100 Hz

Beam spot: 5.5 mm

Ablation depth: 64.89 μm

Fantes' classification

| (Grade) | (Slit lamp biomicroscopic findings on opacity) |
|---|---|
| 0 | Normal |
| 0.5 | Possible to observe opacity under indirect light |
| 1 | Possible to observe opacity under direct light |
| 2 | Possible to observe iris in detail |
| 3 | Difficult to observe iris in detail |
| 4 | Impossible to observe iris in detail |

The results are shown in FIG. 1. The Tranilast group had a lower decrease haze score compared with the control group. Specially, T test showed that haze scores at 3, 5, 6, 7, 8, 9, 10, 11, 12 and 13 days after the surgery were significantly decreased. Accordingly, it was shown that Tranilast had a marked inhibitory effect on corneal subepithelial opacity (haze) after excimer laser treatment. On the other hand, in the steroid group, a decreased haze score was not observed relative to the control group and corneal subepithelial opacity (haze) was not improved.

Industrial Applicability

A pharmaceutical composition comprising as the active ingredient Tranilast has marked inhibitory effect on corneal subepithelial opacity (haze), and is extremely suitable as a corneal subepithelial opacity (haze) inhibitor.

What is claimed is:

1. A method for the prevention or treatment of corneal subepithelial opacity which comprises administering N-(3,4-dimethoxycinnamoyl)anthranilic acid represented by the formula:

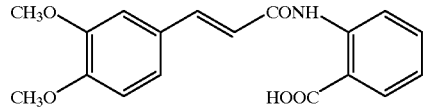

or a pharmaceutically acceptable salt thereof.

2. The method of claim 1, wherein said N-(3,4 dimethoxycinnamoyl) anthranilic acid or pharmaceutically acceptable salt thereof is administered in the form of eye drops.

3. The method of claim 1, wherein said N-(3,4 dimethoxycinnamoyl) anthranilic acid or pharmaceutically acceptable salt thereof is administered in the form of an eye ointment.

4. The method of claim 1, wherein said N-(3,4 dimethoxycinnamoyl) anthranilic acid or pharmaceutically acceptable salt thereof is administered to the eye after eye surgery.

5. The method of claim 4, wherein said surgery is a keratectomy.

6. The method of claim 5, wherein said keratectomy is done by excimer laser.

* * * * *